United States Patent [19]

Takematsu et al.

[11] Patent Number: 5,292,922
[45] Date of Patent: Mar. 8, 1994

[54] N-ACYL-N-PHENYLTETRAHYDROPH-THALAMIC ACID DERIVATIVES, METHODS OF PRODUCING SAME, AND HERBICIDES CONTAINING SAME AS EFFECTIVE COMPONENTS

[75] Inventors: Tetsuo Takematsu, Tochigi; Takashi Kume; Takeo Komata, both of Saitama; Kiyoshi Suzuki, Tochigi; Matsue Minezaki, Saitama; Yumiko Shirakawa, Saitama; Kaoru Mori, Saitama, all of Japan

[73] Assignee: Central Glass Company, Limited, Ube, Japan

[21] Appl. No.: 849,063
[22] PCT Filed: Aug. 21, 1991
[86] PCT No.: PCT/JP91/01109
§ 371 Date: Apr. 22, 1992
§ 102(e) Date: Apr. 22, 1992
[87] PCT Pub. No.: WO92/03407
PCT Pub. Date: Mar. 5, 1992

[30] Foreign Application Priority Data

Aug. 22, 1990 [JP] Japan .................. 2-220892

[51] Int. Cl.$^5$ .............. C07C 229/00; C07C 233/00
[52] U.S. Cl. ......................... 560/47; 560/45; 560/48; 504/341; 504/343; 564/155; 564/158
[58] Field of Search ............. 560/45, 47, 48; 504/341, 342; 564/155, 158

[56] References Cited

U.S. PATENT DOCUMENTS

| | | | |
|---|---|---|---|
| 4,324,580 | 4/1982 | Vogel et al. | 71/118 |
| 4,465,507 | 8/1984 | Konno et al. | 71/98 |

FOREIGN PATENT DOCUMENTS

| | | | |
|---|---|---|---|
| 070326 | 12/1972 | Japan | 560/48 |
| 58-219104A | 12/1983 | Japan . | |
| 162885 | 3/1984 | Japan | 564/155 |
| 172446 | 9/1984 | Japan . | |
| 59-172446A | 9/1984 | Japan . | |

OTHER PUBLICATIONS

Chang, "Preparation of N-substituted tetrahydrophthalimide herbicidal compounds . . ." PCT Int'l Application WO8704049, Jan. 10, 1986, CA 108(5):37640h, the Abstract only.

*Primary Examiner*—José G. Dees
*Assistant Examiner*—Keith MacMillan
*Attorney, Agent, or Firm*—Keck, Mahin & Cate

[57] ABSTRACT

The invention provides N-acyl-N-phenyltetrahydrophthalamic acid derivatives represented by the general formula [I], methods of producing the same, and herbicides containing the same as the effective components,

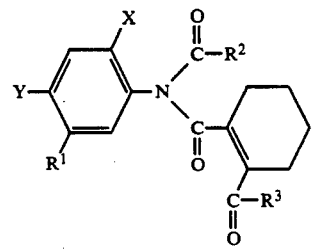

wherein X and Y each individually represent hydrogen atoms or halogen atoms, $R^1$ represents a hydrogen atom, a halogen atom, a lower alkoxy group, a lower alkenyloxy group, a lower alkynyloxy group, a lower alkoxyalkoxy group or a lower alkoxycarbonylalkoxy group, $R^2$ represents a lower alkyl group, a halogenated lower alkyl group, or a substituted or unsubstituted phenyl group, and $R^3$ represents a lower alkoxy group, a lower alkenyloxy group, a lower alkynyloxy group, a lower alkoxyalkoxy group, a benzyloxy group or a lower alkoxycarbonylalkoxy group. The herbicides which are very useful can be widely applied to upland, paddy field, orchard, turf, forest, non-crop land, etc, and are not harmful to crops.

36 Claims, No Drawings

N-ACYL-N-PHENYLTETRAHYDROPH-THALAMIC ACID DERIVATIVES, METHODS OF PRODUCING SAME, AND HERBICIDES CONTAINING SAME AS EFFECTIVE COMPONENTS

TECHNOLOGICAL FIELD

This invention relates to N-acyl-N-phenyltetrahydrophthalamic acid derivatives which are novel compounds, to methods of producing the same, and to herbicides containing the same as the effective components. N-acyl-N-phenyltetrahydrophthalamic acid derivatives of the present invention exhibit excellent herbicidal activity. The derivatives are useful as a herbicide which can be widely applied to upland, paddy field, orchard, pasture, turf, forest, non-crop land, etc. The derivatives are not harmful to crops.

BACKGROUND TECHNOLOGY

Hitherto, herbicidal activity of tetrahydrophthalamic acid derivatives is well known. For example, N-(4'-chlorophenyl)-3,4,5,6-tetrahydrophthalamic acid methyl ester is known, as is disclosed in JP-A (Patent) 48-44425.

However, the conventional tetrahydrophthalamic acid derivatives are not necessarily sufficient in herbicidal activity, or are substantially limited in herbicidal spectrum against weeds. Furthermore, these derivatives are insufficient in selectivity between crops and weeds, thereby inducing problems of safety for crops.

It is an object of the present invention to solve the aforementioned problems, and to provide a novel compounds which are excellent in herbicidal activity but not harmful to crops, methods of producing the same, and herbicides containing the same as the effective components.

DISCLOSURE OF THE INVENTION

The inventors have found that novel tetrahydrophthalamic acid derivatives each having a specific substituent acyl group bonded to an amide nitrogen atom are very excellent in herbicidal activity, selectivity and herbicidal spectrum, and as a result have completed the present invention.

The present invention provides tetrahydrophthalamic acid derivatives represented by the general formula [I], methods of producing the same, and herbicides containing the same as the effective components:

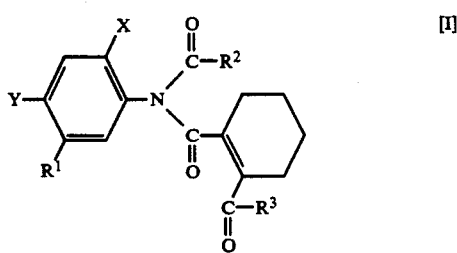

wherein X and Y each individually represent hydrogen atoms or halogen atoms, $R^1$ represents a hydrogen atom, a halogen atom, a lower alkoxy group, a lower alkenyloxy group, a lower alkynyloxy group, a lower alkoxyalkoxy group or a lower alkoxycarbonylalkoxy group, $R^2$ represents a lower alkyl group, a halogenated lower alkyl group or a substituted or unsubstituted phenyl group, and $R^3$ represents a lower alkoxy group, a lower alkenyloxy group, a lower alkynyloxy group, a lower alkoxyalkoxy group, benzyloxy group or a lower alkoxycarbonylalkoxy group.

A compound of the invention can be synthesized, for example, by the following methods.

SYNTHESIS METHOD (a)

A compound of the invention which is represented by the general formula [I] can be synthesized by the reaction of imidoylchloride which is represented by the general formula [II] with a carboxylic acid which is represented by the general formula [III], in a suitable solvent such as benzene, toluene, xylene, methylene chloride, chloroform, ethyl acetate, dioxane, tetrahydrofuran, diethyl ether, dimethylformamide and dimethylsulfoxide, by adding a suitable deacidifying agent such as an organic base such as triethylamine and pyridine or an inorganic base such as potassium hydroxide and sodium hydroxide.

The reaction temperature is usually from 0° C. to 200° C., and a preferred range is from 40° C. to 100° C.

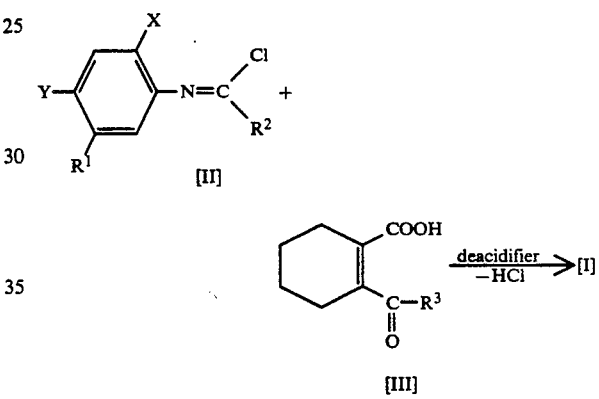

wherein X, Y, $R^1$, $R^2$ and $R^3$ are as defined hereinabove.

SYNTHESIS METHOD (b)

A compound of the invention which is represented by the general formula [I] can be synthesized by the reaction of imidoylchloride which is represented by the general formula [II] with an alkali metal salt of carboxylic acid which is represented by the general formula [IV], in a suitable solvent such as benzene, toluene, xylene, methylene chloride, chloroform, ethyl acetate, dioxane, tetrahydrofuran, diethyl ether, dimethylformamide and dimethylsulfoxide and water, by adding if necessary a phase transfer catalyst such as a quaternary ammonium salt.

The reaction temperature is usually from 0° C. to 200° C., and a preferred range is from 0° C. to 100° C.

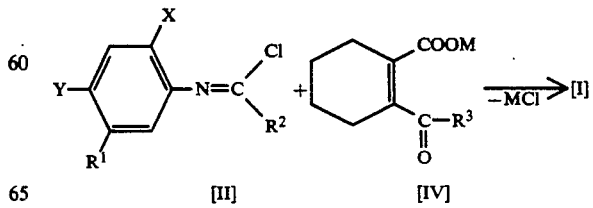

wherein X, Y, $R^1$, $R^2$ and $R^3$ are as defined hereinabove, and "M" represents an alkali metal.

SYNTHESIS METHOD (C)

For synthesizing a compound of the invention which is represented by the general formula [I], firstly, imidoylchloride which is represented by the general formula [II] is produced by the reaction of polymer-carried triphenylphosphine and carbon tetrachloride with an anilide which is represented by the general formula [V] without using any solvent, or in a suitable solvent such as methylene chloride, chloroform, benzene, toluene, xylene, ethyl acetate, ether, dioxane, tetrahydrofuran, N,N-dimethylformamide, N,N-dimethylacetamide, dimethyl sulfoxide and sulfolane. Then, a carboxylic acid which is represented by the general formula [III] and a suitable deacidifying agent such as an organic base such as triethylamine and pyridine or an inorganic base such as potassium hydroxide and sodium hydroxide are reacted with the imidoylchloride, without isolating and refining the imidoylchloride, in a solvent such as methylene chloride, chloroform, benzene, toluene, xylene, cumene, ethyl acetate, ether, dioxane, tetrahydrofuran, N,N-dimethylformamide, N,N-dimethylacetamide, dimethyl sulfoxide, sulfolane, acetone or methylethylketone, or without using any solvent, at a temperature ranging from $-20°$ C. to $250°$ C., and more preferably from $0°$ C. to $100°$ C., thereby synthesizing the compound.

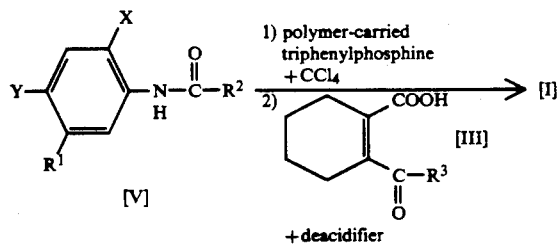

wherein X, Y, $R^1$, $R^2$ and $R^3$ are as defined hereinabove.

Imidoylchloride derivatives which are represented by the general formula [II] and necessary as a starting material to obtain the compound of the present invention which is represented by the general formula [I] can be produced, according to the following reaction formula, by the reaction of anilide derivatives which are represented by the general formula [V], with using a dehydrochlorinating agent, and with using a reaction solvent or not, at a temperature preferably ranging from $0°$ to $100°$ C.

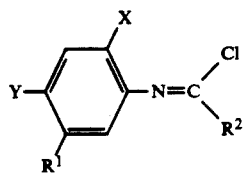

wherein X, Y, $R^1$ and $R^2$ are as defined hereinabove.

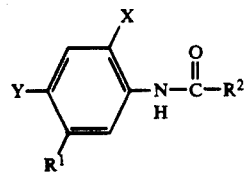

wherein X, Y, $R^1$ and $R^2$ are as defined hereinabove.

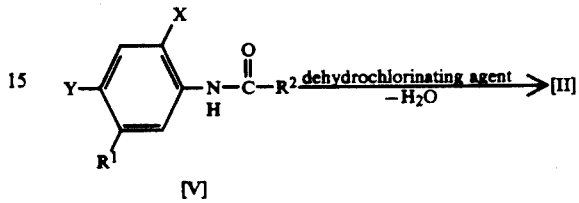

wherein X, Y, $R^1$ and $R^2$ are as defined hereinabove.

As preferable examples of the dehydrochlorinating agent used in the reaction, phosphorus pentachloride, phosphorus trichloride-chlorine, thionyl chloride, arylsulfonylchloride, phosgene, triphenylphosphine-carbon tetrachloride and polymer carried triphenylphosphine-carbon tetrachloride can be cited. Furthermore, as preferable examples of the solvent used in the reaction, halogenated hydrocarbons such as dichloroethane, carbon tetrachloride, chloroform and methylene chloride, aromatic hydrocarbons such as benzene, toluene, xylene and chlorobenzene, and polar solvents such as acetonitrile, dimethyl sulfoxide, etc can be cited.

EXAMPLES

Hereinafter, the present invention is described concretely with respect to examples.

EXAMPLE 1 (according to SYNTHESIS METHOD (a))

Synthesis of N-(2-chloroacetyl)-N-(4-chloro-2-fluoro-5-methoxyphenyl)-3,4,5,6-tetrahydrophthalamic acid methyl ester (A compound which is represented by No. 2 in Table 1 and by the general formula [I])

First, 1.47 g of N-(4-chloro-2-fluoro-5-methoxyphenyl)-2-chloroacetimidoylchloride and 1.00 g of 3,4,5,6-tetrahydrophthalamic acid monomethyl ester were dissolved in 20 ml of benzene, and 570 mg of triethylamine dissolved in 5 ml of benzene was added to the solution at room temperature. After that the stirring was continued for 1.5 hr at $60°$ C. After letting the reaction liquid stand to cool the same, it was poured into iced water, and then the organic layer was separated therefrom. The organic layer was washed first with water and then with saturated brine, and then dried by using anhydrous magnesium sulfate. The solvent was concentrated, and then methanol was added to the residue. The produced crystals were filtered out, then washed with methanol, and then dried to obtain 1.18 g of N-(2-chloroacetyl)-N-(4-chloro-2-fluoro-5-methoxyphenyl)-3,4,5,6-tetrahydrophthalamic acid methyl ester. The melting point was $109°$ C.

EXAMPLE 2 (according to SYNTHESIS METHOD (b))

Synthesis of
N-benzoyl-N-[4-chloro-2-fluoro-5-(1-methylpropargyloxy) phenyl]-3,4,5,6-tetrahydrophthalamic acid methyl ester (A compound which is represented by No. 17 in Table 1 and by the general formula [I])

First, 0.70 g of N-[4-chloro-2-fluoro-5-(1-methylpropargyloxy) phenyl] benzimidoylchloride and 0.47 g of 3,4,5,6-tetrahydrophthalamic acid monomethyl ester potassium salt were mixed in 10 ml of N,N-dimethylformamide, and the stirring under heat was continued for 2 hr at 60° C. After letting the reaction liquid stand to cool the same, it was poured into iced water, and then the organic layer was separated therefrom with benzene and washed first with water and then with saturated brine. Then, it was dried by using anhydrous magnesium sulfate. The solvent was distilled out, and methanol was added to the residue. The precipitated crystals were filtered out, then washed with methanol, and then dried to obtain 0.66 g of N-benzoyl-N-[4-chloro-2-fluoro-5-(1-methylpropargyloxy) phenyl]-3,4,5,6-tetrahydrophthalamic acid methyl ester. The melting point was 119°-124° C.

EXAMPLE 3 (according to SYNTHESIS METHOD (c))

N-(2-chloroacetyl)-N-(4-chloro-2-fluoro-5-methoxycarbonylmethoxyphenyl)-3,4,5,6-tetrahydrophthalamic acid methyl ester (A compound which is represented by No. 9 in Table 1 and by the general formula [I])

First, 0.80 g of N-(4-chloro-2-fluoro-5-methoxycarbonylmethoxyphenyl)-2-chloroacetamide, 1.85 g of polystylene-carried triphenylphosphine (~3 millimols/g) and 3.5 ml of carbon tetrachloride were mixed in 15 ml of 1,2-dichloroethane. The reflux under heat was continued for 45 min. After letting the solution stand to cool the same, polystyrene was filtered out. The solvent of the filtrate was distilled out under reduced pressure. Then, 0.46 g of 3,4,5,6-tetrahydrophthalamic acid monomethyl ester and 7 ml of benzene were added to the residue, and then 0.28 g of triethylamine dissolved in 3 ml of benzene was dropped into the solution at room temperature. The reaction mixture was stirred under heat for 1 hr at 60° C. After letting the mixture stand to cool the same, it was poured into iced water, and then the organic layer was separated therefrom and washed with water. Then, it was dried by using anhydrous magnesium sulfate. The solvent was distilled out, and methanol was added to the residue. The precipitated crystals were filtered out, then washed with methanol, and dried to obtain 0.56 g of N-(2-chloroacetyl)-N-(4-chloro-2-fluoro-5-methoxycarbonylmethoxyphenyl)-3,4,5,6-tetrahydrophthalamic acid methyl ester. The melting point was 144.5°-145.0° C.

EXAMPLE 4

N-(4-chloro-2-fluoro-5-methoxyphenyl)-2-chloroacetimidoylchloride (A compound which is represented by No. 45 in Table 3 and by the general formula [II])

First, 2.00 g of N-(4-chloro-2-fluoro-5-methoxyphenyl)-2-chloroacetamide was mixed with 1.66 g of phosphorus pentachloride, and the stirring was continued for 1.0 hr at 60° C. After letting the mixture stand to cool the same, the produced phosphorus oxychloride was distilled out under reduced pressure. Then, the residue was refined by vacuum distillation to obtain 1.68 g of N-(4-chloro-2-fluoro-5-methoxyphenyl)-2-chloroacetimidoylchloride. The boiling point was 121° C./0.5 mm Hg.

EXAMPLE 5

N-(4-chloro-2-fluoro-5-propargyloxyphenyl)-2-chloroacetimidoylchloride (A compound which is represented by No. 53 in Table 3 and by the general formula [II])

First, 2.00 g of N-(4-chloro-2-fluoro-5-propargyloxyphenyl)-2-chloroacetamide, 4.50 g of triphenylphosphine and 5 ml of carbon tetrachloride were dissolved in 45 ml of 1,2-dichloroethane, and then the reflux under heat was continued for 2 hr. After letting the solution stand to cool the same, the solvent was distilled out under reduced pressure, and then the residue was refined by silica gel column chromatography (effluent: ethyl acetate/n-hexane (v/v)=6/4) to obtain 1.43 g of N-(4-chloro-2-fluoro-5-propargyloxyphenyl)-2-chloroacetimidoylchloride. The boiling point was 144°-146° C./0.4 mm Hg.

EXAMPLE 6

N-[4-chloro-2-fluoro-5-(1-methylpropargyloxy)-phenyl]-acetimidoylchloride (A compound which is represented by No. 57 in Table 3 and by the general formula [II])

First, 7.00 g of N-[4-chloro-2-fluoro-5-(1-methylpropargyloxy)phenyl]-acetamide and 5.62 g of phosphorus pentachloride were mixed in 20 ml of benzene, and the stirring was continued for 1 hr at 60° C. After letting the solution stand to cool the same, benzene and the produced phosphorus oxychloride were distilled out under reduced pressure, and then the residue was refined by vacuum distillation to obtain 5.68 g of N-[4-chloro-2-fluoro-5-(1-methylpropargyloxy)phenyl]-acetimidoylchloride. The boiling point was 104°-105° C./0.11 mm Hg.

Table 1 shows compounds [I] of the present invention each of which was obtained by a process analogous to the processes of the foregoing examples, and Table 2 shows $^1$H-NMR absorption spectrum values thereof. Table 3 shows compounds [II], and Table 4 shows $^1$H-NMR absorption spectrum values thereof. However, the compounds of the present invention are not limited to those shown in Tables 1 to 4.

The compound Nos. in Tables 1 to 4 will be employed in the following examples and experiments.

TABLE 1

| Compound No. | X | Y | $R^1$ | $R^2$ | $R^3$ | m.p. (°C.) |
|---|---|---|---|---|---|---|
| 1 | F | Cl | H | $CH_2Cl$ | $OCH_3$ | oil-like |

TABLE 1-continued

| Compound No. | X | Y | R¹ | R² | R³ | m.p. (°C.) |
|---|---|---|---|---|---|---|
| 2 | | | OCH₃ | | | substance 109 |
| 3 | | | OCH₂CH₃ | | | 115.5–112.5 |
| 4 | | | OCH(CH₃)₂ | | | 88.5–89.5 |
| 5 | | | OCH₂C≡CH | | | 128–129 |
| 6 | | | OCH(CH₃)C≡CH | | OCH₂(CH₂)₂CH₃ | 115–116 |
| 7 | | | OCH₂CH=CH₂ | | OCH₂(CH₂)₂CH₃ | 117.5–118.5 |
| 8 | | | OCH₂OCH₂CH₃ | | | 96.5–97.5 |
| 9 | | | OCH₂COOCH₃ | | | 144.5–145.0 |
| 10 | | | OCH(CH₃)COOCH₃ | | | 140.0–140.5 |
| 11 | | | OCH₃ | CH₃ | OCH₃ | 127–129 |
| 12 | | | | CHClCH₃ | | 120.0–122.5 |
| 13 | | | OCH₂C≡CH | | | 110.5–112.5 |
| 14 | | | OCH₃ | CCl₂CH₃ | | 120–122 |
| 15 | | | | CHClCH₂CH₃ | | 77–80 |
| 16 | | | |  | | 144–148 |
| 17 | | | OCH(CH₃)C≡CH | | | 119–124 |
| 18 | | | OCH₃ | CH₃ | OCH₂C≡CH | 104–105 |
| 19 | | | | | | 67–68 |
| 20 | | | OCH(CH₃)C≡CH | | OCH₃ | 138–139 |
| 21 | | | | | OCH₂(CH₂)₂CH₃ | 57–58 |
| 22 | | | | | OCH₂CH≡CH | 122–124 |
| 23 | | | | | 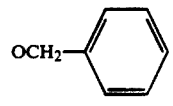 | 99–102 |
| 24 | F | Cl | OCH₃ | CH₂Cl | OCH₂CH₂OCH₃ | 79.0–80.5 |
| 25 | | | | | 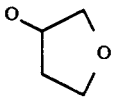 | 116–117 |
| 26 | | | | | 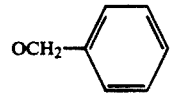 | 89.5–91.0 |
| 27 | | | | | 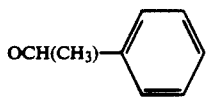 | 93.5–95.0 |
| 28 | | | | | OCH₂COOC₂H₅ | 126.5–127.5 |
| 29 | | | | | OCH(CH₃)COOCH₃ (Rac.) | 92–93 |
| 30 | | | OCH₂C≡CH | CH₂Cl | OCH₂C≡CH | 115–117 |
| 31 | | | | | OCH(CH₃)₂ | 70.5–72.0 |
| 32 | | | | | OCH₂(CH₂)₂CH₃ | 114–115 |
| 33 | | | OCH(CH₃)C≡CH | CH₂Cl | OCH₂C≡CH | 97.5–98.5 |
| 34 | | | | | 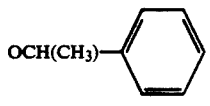 | 67–70 |
| 35 | | | OCH₃ | CH₂Cl | OCH₂CH₃ | 100–101 |
| 36 | | | OCH₂CH₃ | | | 100–102 |
| 37 | | | OCH(CH₃)₂ | | | 92.5–93.5 |
| 38 | | | | | 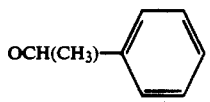 | 108–109 |

TABLE 1-continued

| Compound No. | X | Y | R¹ | R² | R³ | m.p. (°C.) |
|---|---|---|---|---|---|---|
| 39 | | | OCH₃ | | OCH(CH₃)₂ | 86.5–87.5 |
| 40 | | | | | OCH₂C≡CH | 86.5–88.5 |
| 41 | | | OCH(CH₃)₂ | | | 99.0–99.5 |
| 42 | Cl | | H | CH₂Cl | OCH₃ | 100–103 |
| 43 | | | Cl | | | 142–143 |

TABLE 2

| Compound No. | ¹H-NMR Absorprion Spectrum Values (δ ppm) (in CDCl₃) |
|---|---|
| 1 | 1.27–1.70 (m, 4H), 1.98–2.32 (m, 4H), 3.73 (s, 3H), 4.64 (s, 2H), 7.03–7.49 (m, 3H) |
| 2 | 1.30–1.78 (m, 4H), 1.95–2.48 (m, 4H), 3.76 (s, 3H), 3.82 (s, 3H) 4.56 (s, 2H), 7.03 (d, J = 7Hz, 1H), 7.26 (d, J = Hz, 1H) |
| 3 | 1.41 (t, J = 7Hz, 3H), 1.45–1.72 (m, 4H), 2.02–2.42 (m, 4H), 3.77 (s, 3H), 4.00 (q, J = 7Hz, 2H), 4.55 (s, 2H), 7.01 (d, J = 7Hz, 1H), 7.27 (d, J = 9Hz, 1H) |
| 4 | 1.34 (d, J = 6Hz, 6H), 1.42–1.74 (m, 4H), 2.05–2.45 (m, 4H), 3.73 (s, 3H), 4.42 (sep, J = 6Hz, 1H), 4.56 (s, 2H), 7.08 (d, J = 7Hz, 1H), 7.24 (d, J = 9Hz, 1H) |
| 5 | 1.38–1.73 (m, 4H), 2.05–2.43 (m, 4H), 2.51 (t, J = 2Hz, 1H), 3.75 (s, 3H), 4.57 (s, 2H), 4.85 (d, J = 2Hz, 2H), 7.11–7.41 (m, 2H) |
| 6 | 1.35–1.73 (m, 4H), 1.70 (d, J = 7Hz, 3H), 2.03–2.42 (m, 4H), 2.46 (d, J = 2Hz, 1H), 3.74 (s, 3H), 4.53 (s, 2H), 4.82 (dq, J = 7Hz, 1H) 7.19–7.42 (m, 2H) |
| 7 | 1.33–1.78 (m, 4H), 2.05–2.48 (m, 4H), 3.77 (s, 3H), 4.40–4.68 (m, 2H), 4.55 (s, 2H), 5.20–5.60 (m, 2H), 5.80–6.20 (m, 1H), 7.08 d, J = 7Hz, 1H), 7.29 (d, J = 9Hz, 1H) |
| 8 | 1.22 (t, J = 8Hz, 3H), 1.38–1.79 (m, 4H), 2.04–2.44 (m, 4H), 3.75 (q, J = 8Hz, 2H), 3.78 (s, 3H), 4.68 (s, 2H), 5.22 (s, 2H), 7.19–7.48 (m, 2H) |
| 9 | 1.40–1.74 (m, 4H), 2.06–2.40 (m, 4H), 3.77 (s, 3H), 3.80 (s, 3H), 4.53 (s, 2H), 4.66 (s, 2H), 7.08 (d, J = 7Hz, 1H), 7.31 (d, J = 9Hz, 1H) |
| 10 | 1.31–1.77 (m, 4H), 1.65 (d, J = 7Hz, 3H), 2.03–2.44 (m, 4H), 3.76 (s, 3H), 3.79 (s, 3H), 4.50 (s, 2H), 4.72 (q, J = 7Hz, 2H), 7.10 (d, J = 7Hz, 1H), 7.30 (d, J = 9Hz, 1H) |
| 11 | 1.48–1.80 (m, 4H), 2.15–2.49 (m, 4H), 2.24 (s, 3H), 3.74 (s, 3H), 3.88 (s, 3H), 7.12 (d, J = 7Hz, 1H), 7.27 (d, J = 9Hz, 1H) |
| 12 | 1.41–1.87 (m, 4H), 1.65 (d, J = 7Hz, 3H), 2.12–2.50 (m, 4H), 3.72 (s, 3H), 3.85 (s, 3H), 4.71 (brq, J = 7Hz, 1H), 7.11–7.39 (m, 2H) |
| 13 | 1.40–1.90 (m, 4H), 1.65 (d, J = 7Hz, 3H), 2.10–2.53 (m, 4H), 2.55 (t, J = 2Hz, 1H), 3.79 (s, 3H), 4.75 (brq, J = 7Hz, 1H), 4.79 (d, J = 2Hz, 2H), 7.20–7.56 (m, 2H) |
| 14 | 1.59–1.91 (m, 4H), 2.23–2.60 (m, 4H), 2.30 (s, 3H), 3.78 (s, 3H), 3.92 (s, 3H), 7.24 (d, J = 9Hz, 1H), 7.43 (d, J = 7Hz, 1H) |
| 15 | 1.00 (t, J = 7Hz, 3H), 1.40–2.54 (m, 10H), 3.72 (s, 3H), 3.88 (s, 3H), 4.21–4.63 (m, 1H), 7.80–7.40 (m, 2H) |
| 16 | 1.50–1.84 (m, 4H), 2.16–2.70 (m, 4H), 3.75 (2, 3H), 3.90 (s, 3H) 7.04 (d, J = 9Hz,), 7.18–7.70 (m, 6H) |
| 17 | 1.51–1.89 (m, 4H), 1.72 (d, J = 6Hz, 3H), 2.17–2.45 (m, 2H), 2.45–2.69 (m, 2H), 2.57 (d, J = 2Hz, 1H), 3.73 (s, 3H), 4.91 (dq, J = 2.6Hz 1H), 6.99 (d, J = 10Hz, 1H), 11–7.7 (m, 6H) |
| 18 | 1.41–1.82 (m, 4H), 2.05–2.52 (m, 4H), 2.24 (s, 3H), 2.46 (t, J = 2Hz, 1H), 3.88 (s, 3H), 4.75 (d, J = 2Hz, 2H), 7.13 (d, J = 7Hz, 1H), 7.27 (d, J = 9Hz, 1H) |
| 19 | 0.94 (t, J = 7Hz, 3H), 1.11–1.87 (m, 8H), 2.15–2.52 (m, 4H), 2.27 (s, 3H), 3.88 (s, 3H), 4.14 (t, J = 6Hz, 2H), 7.11–7.39 (m, 2H) |
| 20 | 1.43–1.82 (m, 4H), 1.71 (s, 3H), 2.10–2.46 (m, 4H), 2.49 (d, J = 2Hz, 1H), 3.74 (s, 3H), 4.87 (dq, J = 6Hz, 1H), 7.17–7.47 (m, 2H) |
| 21 | 0.94 (t, J = 7Hz, 3H), 1.12–1.86 (m, 8H), 1.71 (d, J = 7Hz, 3H), 2.11–2.47 (m, 4H), 2.25 (s, 3H), 2.49 (d, J = 2Hz, 1H), 4.15 (t, J = 6Hz, 2H), 4.87 (dq, J = 2,7Hz, 1H), 7.17–7.48 (m, 2H) |
| 22 | 1.38–1.86 (m, 4H), 1.72 (d, J = 7Hz, 3H), 2.09–2.60 (m, 6H), 2.24 (s, 3H), 4.77 (d, J = 2Hz, 2H), 4.77 (dq, J = 7Hz, 1H), 7.19–7.47 M, 2H) |
| 23 | 1.45–1.78 (m, 4H), 1.66 (d, J = 7Hz, 3H), 2.10–2.50 (m, 4H), 2.15 (s, 3H), 2.45 (d, J = 2Hz, 1H), 4.75 (dq, J = 2,7Hz, 1H), 5.22 (s, 2H) 7.23 (d, J = 6Hz, 1H), 7.30–7.46 (m, 6H) |
| 24 | 1.31–1.73 (m, 4H), 2.00–2.39 (m, 4H), 3.34 (s, 3H), 3.50–3.70 (m, 2H), 3.81 (s, 3H), 4.12–4.43 (m, 2H, 4.62 (s, 2H), 7.09 (d, J = 7Hz, 1H), 7.25 (d, J = 9Hz, 1H) |
| 25 | 1.38–1.74 (m, 4H), 1.88–2.45 (m, 6H), 3.70–4.00 (m, 4H), 3.84 (s 3H), 4.50 (s, 2H), 5.25–5.49 (m, 1H), 7.15 (d, J = 7Hz, 1H), 7.29 (d J = 9Hz, 1H) |
| 26 | 1.39–1.73 (m, 4H), 2.08–2.47 (m, 4H), 3.65 (s, 3H), 4.50 (s, 2H), |

TABLE 2-continued

| Compound No. | ¹H-NMR Absorprion Spectrum Values (δ ppm) (in CDCl₃) |
|---|---|
|  | 5.21 (s, 2H), 6.96 (d, J = 7Hz, 1H), 7.28 (d, J = 9Hz, 1H), 7.28–7.65 (m, 5H) |
| 27 | 1.31–1.73 (m, 4H), 1.55 (d, J = 6Hz, 3H), 2.00–2.46 (m, 4H), 3.48 (s, 3H), 4.51 (s, 2H), 5.95 (q, J = 6Hz, 1H), 6.90 (d, J = 7Hz, 1H), 7.21 (d, J = 9Hz, 1H), 7.24–7.44 (m, 5H) |
| 28 | 1.29 (t, J = 8Hz, 3H), 1.33–1.75 (m, 4H), 2.01–2.48 (m, 4H), 3.85 (s, 3H), 4.22 (q, J = 8Hz, 2H), 4.60 (s, 2H), 4.69 (s, 2H), 7.10 (d, J = 7Hz, 1H), 7.28 (d, J = 9Hz, 1H) |
| 29 | 1.35–1.73 (m, 4H), 1.53 (d, J = 7Hz, 3H), 2.05–2.48 (m, 4H), 3.76 (s, 3H), 3.86 (s, 3H), 4.62 (s, 2H), 5.18 (q, J = 7Hz, 1H), 7.13 (d, J = 7Hz, 1H), 7.29 (d, J = 9Hz, 1H) |
| 30 | 1.35–1.81 (m, 4H), 2.00–2.45 (m, 4H), 2.55 (t, J = 2Hz, 1H), 2.57 (t, J = 2Hz, 1H), 4.60 (s, 2H), 4.73 (d, J = 2Hz, 2H), 4.77 (d, J = 2Hz, 2H), 7.17 (d, J = 7Hz, 1H), 7.27 (d, J = 9Hz, 1H) |
| 31 | 1.31 (d, J = 7Hz, 6H), 1.35–1.76 (m, 4H), 2.08–2.49 (m, 4H), 2.55 (t, J = 2Hz, 1H), 4.61 (s, 2H), 4.73 (d, J = 2Hz, 2H), 5.09 (sep, J = 7Hz, 1H), 7.21–7.45 (m, 2H) |
| 32 | 0.94 (t, J = 7Hz, 3H), 1.14–1.83 (m, 8H), 2.06–2.42 (m, 4H), 2.42 (t, J = 2Hz, 1H), 4.17 (t, J = 7Hz, 2H), 4.57 (s, 3H), 4.72 (d, J = 2Hz 2H, 7.17–7.40 (m, 2H) |
| 33 | 1.41–1.90 (m, 4H), 1.73 (d, J = 7Hz, 3H), 2.10–2.48 (m, 4H), 2.48–2.65 (m, 2H), 4.64 (s, 2H), 4.79 (d, J = 2Hz, 2H), 4.82 (dq, J = 2,7Hz 1H), 7.21–7.45 (m, 2H) |
| 34 | 1.30–1.77 (m, 10H), 2.05–2.45 (m, 4H), 2.44 (d, J = 2Hz, 1H), 4.48 (s, 2H), 4.64 (dq, J = 2,7Hz, 1H), 5.98 (q, J = 7Hz, 1H), 7.11–7.47 (m, 7H) |
| 35 | 1.26 (t, J = 8Hz, 3H), 1.37–1.77 (m, 4H), 2.10–2.43 (m, 4H), 3.79 s, 3H), 4.18 (q, J = 8Hz, 2H), 4.56 (s, 2H), 7.05 (d, J = 7Hz, 1H), 7.39 (d, J = 9Hz, 1H) |
| 36 | 1.29 (t, J = 7Hz, 3H), 1.36–1.74 m, (4H), 1.43 (t, J = 7Hz, 3H), 2.03–2.41 (m, 4H), 3.99 (q, J = 7Hz, 2H), 4.20 (q, J = 7Hz, 2H), 4.58 (s, 2H), 7.04 (d, J = 7Hz, 1H), 7.35 (d, J = 9Hz, 1H) |
| 37 | 1.30 (t, J = 7Hz, 3H), 1.34 (d, J = 6Hz, 6H), 1.41 (m, 4H), 2.04–2.36 (m, 4H), 4.20 (q, J = 7Hz, 2H), 4.39 (sep, J = 6Hz, 1H), 4.59 (s, 3H), 7.10 (d, J = 7Hz, 1H), 7.24 (d, J = 9Hz, 1H) |
| 38 | 1.08–1.37 (m, 6H), 1.40–1.74 (m, 4H), 1.59 (d, J = 7Hz, 3H), 2.08–2.46 (m, 4H), 4.21 (sep, J = 6Hz, 1H), 4.49 (s, 2H), 5.94 (q, J = 7Hz 1H), 7.01 (d, J = 7Hz, 1H), 7.22 (d, J = 9Hz, 1H), 7.36–7.46 (m, 5H) |
| 39 | 1.27 (d, J = 6Hz, 6H), 1.36–1.69 (m, 4H), 2.00–2.37 (m, 4H), 3.82 (s, 3H), 4.63 (s, 2H), 5.08 (sep, J = 7Hz, 1H), 7.09 (d, J = 7Hz, 1H) 7.28 (d, J = 9Hz, 1H) |
| 40 | 1.35–1.74 (m, 4H), 2.08–2.44 (m, 4H), 2.52 (t, J = 2Hz, 1H), 3.83 (s, 3H), 4.58 (s, 2H), 4.78 (d, J = 2Hz, 2H), 7.04 (d, J = 7Hz, 1H) 7.29 (d, J = 9Hz, 1H) |
| 41 | 1.35 (d, J = 6Hz, 6H), 1.40–1.71 (m, 4H), 2.10–2.32 (m, 4H), 2.50 (t, J = 2Hz, 1H), 4.44 (sep, J = 6Hz, 1H), 4.57 (s, 2H), 4.76 (d, J = 2Hz, 2H), 7.08 (d, J = 7Hz, 1H), 7.27 (d, J = 9Hz, 1H) |
| 42 | 1.43–1.89 (m, 4H), 2.17–2.53 (m, 4H), 3.73 (s, 3H), 4.22 (s, 2H), 7.35–7.72 (m, 3H) |
| 43 | 1.32–1.85 (m, 4h), 2.13–2.48 (m, 4H), 3.78 (s, 3H), 4.24 (brs, 2H), 7.68 (s, 1H), 7.78 (s, 1H) |

TABLE 3

| Compound No. | X | Y | R₁ | R₂ | b.p. (°C.) (mm Hg) |
|---|---|---|---|---|---|
| 44 | F | Cl | H | CH₂Cl | 86 (0.5) |
| 45 |   |   | OCH₃ |   | 121 (0.5) |
| 46 |   |   |   | CH₃ | 100–101 (0.15) |
| 47 |   |   |   | CHClCH₃ | — |
| 48 |   |   |   | CHClCH₂CH₃ | — |
| 49 |   |   |   | CCl₂CH₃ | — |
| 50 |   |   |   |   | — |
| 51 |   |   | OCH₂CH₃ | CH₂Cl | 133 (0.45) |
| 52 |   |   | OCH(CH₃)₂ |   | 126 (0.21) |
| 53 |   |   | OCH₂C≡CH |   | 144–146 (0.4) |
| 54 |   |   |   | CHClCH₃ | — |
| 55 |   |   | OCH(CH₃)C≡CH | CH₂Cl | 142 (0.5) |
| 56 |   |   |   |   | — |
| 57 |   |   |   | CH₃ | 104–105 (0.11) |
| 58 |   |   | OCH₂CH=CH₂ | CH₂Cl | — |
| 59 |   |   | OCH₂OCH₂CH₃ |   | — |
| 60 |   |   | OCH₂COOCH₃ |   | — |
| 61 |   |   | OCH(CH₃)COOCH₃ |   | — |
| 62 | Cl |   | H |   | 116 (0.5) |

TABLE 3-continued

| Compound No. | X | Y | R₁ | R₂ | b.p. (°C.) (mm Hg) |
|---|---|---|---|---|---|
| 63 | | Cl | | | — |

TABLE 4

| Compound No. | ¹H-NMR Absorption Spectrum Values (δ ppm) (in CDCl₃) |
|---|---|
| 45 | 3.88(s, 3H), 4.49(s, 2H), 6.55(d, J=7Hz, 1H), 7.22(d, J=9Hz, 1H) |
| 46 | 2.58(s, 3H), 3.82(s, 3H), 6.50(d, J=7Hz, 1H), 7.20(d, J=9Hz, 1H) |
| 47 | 1.83(d, J=7Hz, 3H), 3.82(s, 3H), 4.85(q, J=7Hz, 1H), 6.51(d, J=7Hz, 1H), 7.18(d, J=9Hz, 1H) |
| 48 | 1.13(t, J=8Hz, 3H), 2.00 -2.35(m, 2H), 3.90(s, 3H), 4.63 (t, J=7Hz, 1H), 6.50(d,J=7Hz, 1H), 7.20(d, J=9Hz, 1H) |
| 49 | 2.55(s, 3H), 3.88(s, 3H), 6.57(d, J=7Hz, 1H), 7.25(d, J=9Hz, 1H) |
| 50 | 3.87(s, 3H), 6.62(d, J=7Hz, 1H), 7.24(d, J=9Hz, 1H), 7.34–7.68(m, 3H), 8.08–8.34(m, 2H) |
| 51 | 1.45(t, J=7Hz, 3H), 4.04(q, J=7Hz, 2H), 4.49(s, 3H), 6.54(d, J=7Hz, 1H), 7.20(d, J=9Hz, 1H) |
| 52 | 1.37(d, J=6Hz, 6H), 4.44(sep, J=6Hz, 1H), 4.48(s, 2H), 6.58(d, J=7Hz, 1H), 7.19(d, J=9Hz, 1H) |
| 53 | 2.55(t, L=2Hz, 1H), 4.43(s, 2H), 4.71(d, J=2Hz, 2H), 6.72(d, J=7Hz, 1H), 7.20(d, J=9Hz, 1H) |
| 55 | 1.70(d, J=7Hz, 3H), 2.52(d, J=2Hz, 1H), 4.49(s, 3H), 4.83 (dq, J=2, 7Hz, 1H), 6.80(d, J=7Hz, 1H), 7.23(d, J=9Hz, 1H) |
| 56 | 1.69(d, J=7Hz, 3H), 2.48(d, J=2Hz, 1H), 4.81 (dq, J=2, 7Hz, 1H), 6.87(d, J=7Hz, 1H), 7.20 (d, J=9Hz, 1H), 7.31–7.65(m, 3H), 8.08–8.22(m, 2H) |
| 57 | 1.70(d, J=7Hz, 3H), 2.50(d, J=2Hz, 1H), 2.61(s, 3H), 4.81 (dq, J=2, 7Hz, 1H), 6.87(d, J=7Hz, 1H), 7.18(d, J=9Hz, 1H) |
| 59 | 1.33(t, J=8Hz, 3H), 3.77(q, J=8Hz, 2H), 4.49(s, 2H), 5.22 (s, 2H), 6.87(d, J=7Hz, 1H), 7.21(d, J=9Hz, 1H) |
| 62 | 4.48(s, 2H), 6.82(d, J=9Hz, 1H), 7.27(dd, J=2, 8Hz, 1H), 7.44(d, J=2Hz, 1H) |

A herbicide of the present invention containing a compound of the present invention as the effective component has herbicidal activity against various weeds causing problems upon the submerged soil treatment in paddy fields, such as gramineous weeds such as *nobie* (barnyardgrass, *Echinochloa* spp.), broad-leaved weeds such as *azena* (flase pimpernel, *Lindernia pyxidaria*), *kikashigusa* (toothcup, *Rotala indica*), *mizohakobe* (waterwort, *Elatine triandra*), cyperaceous weeds such as *tamagayatsuri* (small-flowered umbrellaplant, *Cyperus difformis*) and *hotarui* (bulrush, *Scirpus juncoides*), and weeds such as *konagi* (*Monochoria vaginalis*). Furthermore, the herbicide has herbicidal activity against various weeds causing problems upon the foliage treatment and the soil treatment in uplands, such as broad-leaved weeds such as *karashina* (indian mustard, *Brassica juncea*), *aobiyu* (slender amaranth, *Amaranthus viridis*), *hakobe* (chickweed, *Stellaria media*), *shiroza* (common lambsquarters, *Chenopodium album*), *onamomi* (heartleaf cocklebur, *Xanthium strumarium*), *marubaasagao* (tall morningglory, *Ipomoea purpurea*), *yaemugura* (catchweed bedstraw, *Galium aparine*), *suberihiyu* (common purslane, *Portulaca oleracea*), *ichibi* (velvetleaf, *Abutilon theophrasti*), *amerika-tsunokusanemu* (hemp sesbania, *Sesbania exaltata*), *ebisugusa* (sicklepod, *Cassia obtusifolia*), *inuhouzuki* (black nightshade, *Solanum nigrum*), spedwells, smart weeds, violets, *tade* (*Persicaria longiseta*) and its relatives, and *sumire* (*Viola mandshurica*) and its relatives, gramineous weeds such as *inubie* (barnyardgrass, *Echinochloa crus-galli*), *enokorogusa* (green foxtail, *Setaria viridis*) and *karasumugi* (wild oat, *Avena fatua*), and cyperaceous weeds such as *mehishiba* (henry crabgrass, *Digitaria ciliaris*), *seibanmorokoshi* (johnsongrass, *Sorghum halepense*) and *enbaku* (oat, *Avena sativa*), and commelinaceous weeds such as *tsuyukusa* (dayflower, *Commelina communis*). The herbicide of the present invention hardly injures major crops such as rice, wheat, corn and soybean.

Therefore, the herbicide of the present invention can be applied to upland, paddy field, orchard, pasture, turf, forest and non-crop land.

It is possible to process the herbicide of the present invention into an arbitrary form such as wettable powder, emulsion, granules, powder or flowable by using the effective components which are the abovementioned compounds of the present invention and a pesticide adjuvant which is generally used in this field, such as an inactive solid carrier or liquid carrier and/or an emulsifying and dispersing agent. As the inactive carriers, for example, talc, clay, bentonite, kaolin, diatomaceous earth, calcium carbonate, wood flour, starch, gum arabic, water, alcohol, kerosene, benzene, xylene, n-hexane, acetone, dimethylformamide, glycol ether, N-methylpyrrolidone can be cited. Besides, it is possible to adequately incorporate auxiliary agents for formulation, such as spreader, diluent, surfactant and solvent.

Upon using the compound of the present invention, a suitable application dosage is variable according to related factors such as manner of application, object of application, time of application and occurrence condition of weeds, but in general the application dosage, as expressed as the amount of the effective component, is from 0.1 to 300 g, and preferably from 1 to 300 g, per 10 ares.

Furthermore, to use the herbicide containing the compound of the present invention, it may be mixed with other herbicides, plant growth regulators, fungicides, insecticides, other pesticides, fertilizers and soil conditioners.

The following are examples of herbicides according to the present invention, though compounds, carriers, adjuvants and the proportions of the ingredients are not limited to those in these examples. In these examples the amount of each component is indicated by parts by weight.

EXAMPLE 7 (Wettable Powder)

| | |
|---|---|
| Compound No. 1 | 10 parts |
| Soidum lignin sulfonate | 1.5 parts |
| Polyoxyethylene alkylaryl ether | 1.5 parts |
| Clay | 87 parts |

These materials were mixed together until a uniform mixture was obtained, and the mixture was pulverized to obtain a wettable powder.

EXAMPLE 8 (GRANULES)

| | |
|---|---|
| Compound No. 1 | 7 parts |

-continued

| Bentonite | 30 parts |
| Sodium alkylsulfonate | 2 parts |
| Clay | 61 parts |

These materials were mixed together and kneaded until a uniform mixture was obtained, and the mixture was granulated by an ordinary granulation method thereby to obtain granules.

The following experiments are illustrative of the herbicidal effects of the compounds of the present invention.

EXPERIMENT 1 (FLOODED SOIL TREATMENT)

Paddy soil (clay loam) was put into a pot so as to have a surface area of 1/15500 ares. Uniformly mixed seeds of several kinds of weeds, viz., nobie (barnyardgrass, Echinochloa spp.), broad-leaved weeds, hotarui (bulrush, Scirpus juncoides), tamagayatsuri (small-flowered umbrellaplant, Cyperus difformis) and konagi (monochoria, Monochoria vaginalis), were sown in the surface layer of the soil in each pot, and then paddy rice seedlings at the two- or three-leaved stage were transplanted into each pot to a depth of 2 cm, and water was fed into each pot so as to provide a 3 cm deep water layer on the soil surface. After 3 days, in other words at the initial stage of germination of nobie (barnyardgrass, Echinochloa spp.), a predetermined amount of a selected compound in the form of diluted aqueous solution was dropped into the water layer in each pot. After that, the pots were kept in a glass chamber to allow the paddy rice and the weeds to grow, and after the lapse of 4 weeks from the treatment with the selected compounds, the herbicidal effects and the degree of injury to the paddy rice were evaluated. The results are shown in Table 5. In the table, the herbicidal effects and the degree of injury to the paddy rice are indicated by numerical values, which have the following meaning.

5: completely killed
4: seriously injured
3: considerably injured
2: somewhat injured
1: slightly injured
0: not injured (normally grown)

EXPERIMENT 2 (FOLIAGE TREATMENT)

Upon seedling stage (two- or three-leaved stage) of rice, cockspur (Panicum crus-galli), garden radish, aobiyu (slender amaranth, Amaranthus viridis) and mehishiba (henry crabgrass, Digitaria cliaris) which were grown on a cultivated soil put in pots of 1/15500 ares, a selected compound in suspended wettable powder was sprayed to each plant. After that, the pots were kept in a glass chamber to allow each plant to grow, and after the lapse of 4 weeks from the treatment with the selected compounds the herbicidal effects were evaluated. The results are shown in Table 6. The evaluation of the herbicidal effects was similarly conducted as to that of Experiment 1.

TABLE 5

| Compound No. | Quantity of Compound g/10 a | Injury of Paddy | Herbicidal Effect | | | | |
|---|---|---|---|---|---|---|---|
| | | | nobie | broad-leaved weed | hotarui | tamagayatsuri | kinagi |
| 2 | 6.25 | 0 | 4.5 | 5 | 4.5 | 5 | 5 |
|   | 3.125 | 0 | 4 | 5 | 4 | 4 | 5 |
| 3 | 6.25 | 1 | 5 | 5 | 5 | 5 | 5 |
|   | 3.125 | 0 | 4.5 | 5 | 4 | 5 | 5 |
| 4 | 6.25 | 0 | 5 | 5 | 5 | 5 | 5 |
|   | 3.125 | 0 | 5 | 5 | 5 | 5 | 5 |
| 5 | 6.25 | 1 | 5 | 5 | 5 | 5 | 5 |
|   | 3.125 | 0 | 5 | 5 | 5 | 5 | 5 |
| 6 | 6.25 | 0 | 5 | 5 | 5 | 5 | 5 |
|   | 3.125 | 0 | 5 | 5 | 5 | 5 | 5 |
| 7 | 6.25 | 0 | 5 | 5 | 5 | 5 | 5 |
|   | 3.125 | 0 | 5 | 5 | 4.5 | 5 | 5 |
| 12 | 6.25 | 0 | 5 | 5 | 5 | 5 | 5 |
|   | 3.125 | 0 | 4.5 | 5 | 4.5 | 5 | 5 |
| 13 | 6.25 | 0 | 5 | 5 | 5 | 5 | 5 |
|   | 3.125 | 0 | 5 | 5 | 4.5 | 5 | 5 |
| 15 | 6.25 | 0 | 4 | 5 | 4 | 5 | 5 |
|   | 3.125 | 0 | 3 | 5 | 3 | 5 | 5 |
| 30 | 6.25 | 0 | 5 | 5 | 5 | 5 | 5 |
|   | 3.125 | 0 | 5 | 5 | 5 | 5 | 5 |
| 31 | 6.25 | 0 | 5 | 5 | 5 | 5 | 5 |
|   | 3.125 | 0 | 5 | 5 | 5 | 5 | 5 |
| 32 | 6.25 | 0 | 5 | 5 | 3 | 5 | 5 |
|   | 3.125 | 0 | 5 | 5 | 3 | 5 | 5 |
| 37 | 6.25 | 1 | 5 | 5 | 5 | 5 | 5 |
|   | 3.125 | 0 | 5 | 5 | 5 | 5 | 5 |
| 39 | 6.25 | 0 | 5 | 5 | 5 | 5 | 5 |
|   | 3.125 | 0 | 4.5 | 5 | 4 | 5 | 5 |
| Comparative agent A | 6.25 | 0 | 4 | 4.5 | 4.5 | 5 | 5 |
|   | 3.125 | 0 | 2 | 2 | 1 | 4.5 | 4 |

Comparative agent A-MO

TABLE 6

| Compound No. | Quantity of Compound g/10 a | rice | cockspur | garden radish | aobiyu | mehishiba |
|---|---|---|---|---|---|---|
| 2 | 16 | 1 | 0 | 5 | 5 | 3 |
|   | 8  | 1 | 0 | 4 | 5 | 1 |
| 3 | 16 | 3 | 3 | 5 | 5 | 4.5 |
|   | 8  | 2 | 2 | 5 | 5 | 3 |
| 4 | 16 | 2 | 0 | 5 | 5 | 3 |
|   | 8  | 2 | 0 | 4 | 5 | 1 |
| 5 | 16 | 3 | 3 | 5 | 5 | 4 |
|   | 8  | 2 | 2 | 5 | 5 | 4.5 |
| 6 | 16 | 4.5 | 3 | 5 | 5 | 5 |
|   | 8  | 4.5 | 3 | 5 | 5 | 4.5 |
| 7 | 16 | 0 | 0 | 5 | 5 | 0 |
|   | 8  | 0 | 0 | 5 | 5 | 0 |
| 8 | 16 | 0.5 | 0 | 5 | 5 | 0 |
|   | 8  | 0.5 | 0 | 5 | 5 | 0 |
| 13 | 16 | 0.5 | 0 | 5 | 5 | 0 |
|    | 8  | 0.5 | 0 | 5 | 5 | 0 |
| 19 | 16 | 0.5 | 0 | 5 | 5 | 0 |
|    | 8  | 0.5 | 0 | 5 | 5 | 0 |
| 25 | 16 | 5 | 3 | 5 | 5 | 5 |
|    | 8  | 5 | 3 | 5 | 5 | 3 |
| 29 | 16 | 5 | 3 | 5 | 5 | 5 |
|    | 8  | 5 | 3 | 5 | 5 | 5 |
| 33 | 16 | 0.5 | 0 | 5 | 5 | 0 |
|    | 8  | 0.5 | 0 | 5 | 5 | 0 |
| 34 | 16 | 0.5 | 0 | 5 | 5 | 0 |
|    | 8  | 0.5 | 0 | 5 | 5 | 0 |
| 35 | 16 | 4 | 3 | 5 | 5 | 4 |
|    | 8  | 3 | 3 | 5 | 5 | 4 |
| 39 | 16 | 1 | 1 | 5 | 5 | 3 |
|    | 8  | 1 | 0 | 5 | 5 | 1 |
| Comparative agent B | 16 | 0 | 0 | 0 | 4 | 1 |
|  | 8 | 0 | 0 | 0 | 3 | 0 |

Comparative agent B-PROPANOL

MERITS OF THE INVENTION

N-acyl-N-phenyltetrahydrophthalamic acid derivatives of the present invention, which are novel compounds, exhibit excellent herbicidal activity. These derivatives provide a herbicide which can be widely applied to upland, paddy field, orchard, turf, forest, non-crop land, etc, and which is not harmful to crops.

We claim:

1. N-acyl-N-phenyltetrahydrophthalamic acid derivatives represented by the general formula (I),

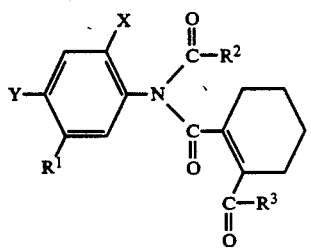

[I]

wherein X and Y each individually represent hydrogen atoms or halogen atoms, $R^1$ represents a hydrogen atom, a halogen atom, a lower alkoxyl group, a lower alkenyloxy group, a lower alkynyloxy group, a lower alkoxyalkoxy group or a lower alkoxycarbonylalkoxy group, $R^2$ represents a lower alkyl group, a halogenated lower alkyl group, or a substituted or unsubstituted phenyl group, and $R^3$ represents a lower alkoxy group, a lower alkenyloxy group, a lower alkynyloxy group, a lower alkoxyalkoxy group, benzyloxy group or a lower alkoxycarbonylalkoxy group.

2. Method of producing N-acyl-N-phenyltetrahydrophthalamic acid derivatives which are represented by the general formula [I], as defined above, by the reaction of imidoylchloride derivatives represented by the general formula [II], in the presence of a base, with a carboxylic acid represented by the general formula [III],

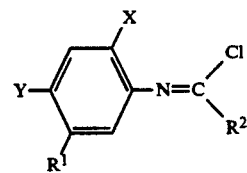

[II]

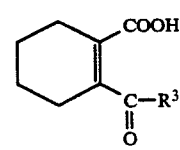

[III]

wherein X, Y, $R^1$, $R^2$ and $R^3$ are as defined hereinabove.

3. Method of producing N-acyl-N-phenyltetrahydrophthalamic acid derivatives which are represented by the general formula [I], as defined above, by the reaction of imidoylchloride which is represented by the general formula [II] with an alkali metal salt of carboxylic acid which is represented by the general formula [IV],

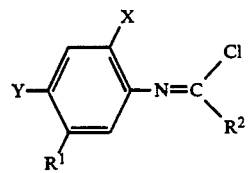

[II]

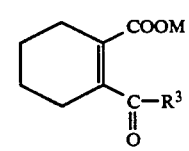

[IV]

wherein X, Y, $R^1$ $R^2$ and $R^3$ are as defined hereinabove, and M is an alkali metal.

4. A herbicide comprising, as effective components, N-acyl-N-phenyltetrahydrophthalamic acid derivatives which are represented by the general formula [I],

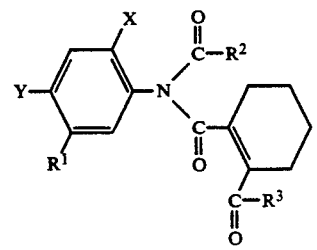

[I]

wherein X, Y, $R^1$, $R^2$ and $R^3$ are as defined hereinabove.

5. A herbicide according to claim 4, which is in the form of a wettable powder comprising an inactive carrier.

6. A herbicide according to claim 4, which is in the form of granules comprising an inactive carrier.

7. A herbicide according to claim 4, which is in the form of an emulsion comprising an inactive carrier.

8. A herbicide according to claim 4, wherein said N-acyl-N-phenyltetrahydrophthalamic acid derivative is N-(2-chloroacetyl)-N-(4-chloro-2-fluoro-5-methoxyphenyl)-3,4,5,6-tetrahydrophthalamic acid methyl ester.

9. A herbicide according to claim 4, wherein said N-acyl-N-phenyltetrahydrophthalamic acid derivative is N-(2-chloroacetyl)-N-(4-chloro-2-fluoro-5-isopropoxyphenyl)-3,4,5,6-tetrahydrophthalamic acid methyl ester.

10. A herbicide according to claim 4, wherein said N-acyl-N-phenyltetrahydrophthalamic acid derivative is N-(2-chloroacetyl)-N-(4-chloro-2-fluoro-5-propargyloxyphenyl)-3,4,5,6-tetrahydrophthalamic acid methyl ester.

11. A herbicide according to claim 4, wherein said N-acyl-N-phenyltetrahydrophthalamic acid derivative is N-(2-chloroacetyl)-N-[4-chloro-2-fluoro-5-(1-methylpropargyloxy) phenyl]-3,4,5,6-tetrahydrophthalamic acid methyl ester.

12. A herbicide according to claim 4, wherein said N-acyl-N-phenyltetrahydrophthalamic acid derivative is N-(2-chloroacetyl)-N-(4-chloro-2-fluoro-5-allyloxyphenyl)-3,4,5,6-tetrahydrophthalamic acid methyl ester.

13. A herbicide according to claim 4, wherein said N-acyl-N-phenyltetrahydrophthalamic acid derivative is N-(2-chloroacetyl)-N-(4-chloro-2-fluoro-5-ethoxymethoxyphenyl)-3,4,5,6-tetrahydrophthalamic acid methyl ester.

14. A herbicide according to claim 4, wherein said N-acyl-N-phenyltetrahydrophthalamic acid derivative is N-(2-chloroacetyl)-N-(4-chloro-2-fluoro-5-methoxycarbonylmethoxyphenyl)-3,4,5,6-tetrahydrophthalamic acid methyl ester.

15. A herbicide according to claim 4, wherein said N-acyl-N-phenyltetrahydrophthalamic acid derivative is N-(2-chloropropionyl)-N-(4-chloro-2-fluoro-5-propargyloxyphenyl)-3,4,5,6-tetrahydrophthalamic acid methyl ester.

16. A herbicide according to claim 4, wherein said N-acyl-N-phenyltetrahydrophthalamic acid derivative is N-benzoyl-N-[4-chloro-2-fluoro-5-(1-methylpropargyloxy)phenyl]-3,4,5,6-tetrahydrophthalamic acid methyl ester.

17. A herbicide according to claim 4, wherein said N-acyl-N-phenyltetrahydrophthalamic acid derivative is N-acetyl-N-(4-chloro-2-fluoro-5-methoxyphenyl)-3,4,5,6-tetrahydrophthalamic acid propargyl ester.

18. A herbicide according to claim 4, wherein said N-acyl-N-phenyltetrahydrophthalamic acid derivative is N-acetyl-N-(4-chloro-2-fluoro-5-methoxyphenyl)-3,4,5,6-tetrahydrophthalamic acid n-butyl ester.

19. A herbicide according to claim 4, wherein said N-acyl-N-phenyltetrahydrophthalamic acid derivative is N-acetyl-N-[4-chloro-2-fluoro-5-(1-methylpropargyloxy)phenyl]-3,4,5,6-tetrahydrophthalamic acid methyl ester.

20. A herbicide according to claim 4, wherein said N-acyl-N-phenyltetrahydrophthalamic acid derivative is N-acetyl-N-[4-chloro-2-fluoro-5-(1-methylpropargyloxy)phenyl]-3,4,5,6-tetrahydrophthalamic acid n-butyl ester.

21. A herbicide according to claim 4, wherein said N-acyl-N-phenyltetrahydrophthalamic acid derivative is N-acetyl-N-[4-chloro-2-fluoro-5-(1-methylpropargyloxy)phenyl]-3,4,5,6-tetrahydrophthalamic acid propargyl ester.

22. A herbicide according to claim 4, wherein said N-acyl-N-phenyltetrahydrophthalamic acid derivative is N-acetyl-N-[4-chloro-2-fluoro-5-(1-methylpropargyloxy)phenyl]-3,4,5,6-tetrahydrophthalamic acid benzyl ester.

23. A herbicide according to claim 4, wherein said N-acyl-N-phenyltetrahydrophthalamic acid derivative is N-(2-chloroacetyl)-N-(4-chloro-2-fluoro-5-methoxyphenyl)-3,4,5,6-tetrahydrophthalamic acid methoxyethyl ester.

24. A herbicide according to claim 4, wherein said N-acyl-N-phenyltetrahydrophthalamic acid derivative is N-(2-chloroacetyl)-N-(4-chloro-2-fluoro-5-methoxyphenyl)-3,4,5,6-tetrahydrophthalamic acid α-methylbenzyl ester.

25. A herbicide according to claim 4, wherein said N-acyl-N-phenyltetrahydrophthalamic acid derivative is N-(2-chloroacetyl)-N-(4-chloro-2-fluoro-5-methoxyphenyl)-3,4,5,6-tetrahydrophthalamic acid (1-methoxycarbonyl)ethyl ester.

26. A herbicide according to claim 4, wherein said N-acyl-N-phenyltetrahydrophthalamic acid derivative is N-(2-chloroacetyl)-N-(4-chloro-2-fluoro-5-propargyloxyphenyl)-3,4,5,6-tetrahydrophthalamic acid propargyl ester.

27. A herbicide according to claim 4, wherein said N-acyl-N-phenyltetrahydrophthalamic acid derivative is N-(2-chloroacetyl)-N-(4-chloro-2-fluoro-5-propargyloxyphenyl)-3,4,5,6-tetrahydrophthalamic acid isopropyl ester.

28. A herbicide according to claim 4, wherein said N-acyl-N-phenyltetrahydrophthalamic acid derivative is N-(2-chloroacetyl)-N-[4-chloro-2-fluoro-5-(1-methylpropargyloxy)phenyl]-3,4,5,6-tetrahydrophthalamic acid propargyl ester.

29. A herbicide according to claim 4, wherein said N-acyl-N-phenyltetrahydrophthalamic acid derivative is N-(2-chloroacetyl)-N-[4-chloro-2-fluoro-5-(1-methylpropargyloxy)phenyl]-3,4,5,6-tetrahydrophthalamic acid α-methylbenzyl ester.

30. A herbicide according to claim 4, wherein said N-acyl-N-phenyltetrahydrophthalamic acid derivative is N-(2-chloroacetyl)-N-(4-chloro-2-fluoro-5-methoxyphenyl)-3,4,5,6-tetrahydrophthalamic acid ethyl ester.

31. A herbicide according to claim 4, wherein said N-acyl-N-phenyltetrahydrophthalamic acid derivative is N-(2-chloroacetyl)-N-(4-chloro-2-fluoro-5-ethoxyphenyl)-3,4,5,6-tetrahydrophthalamic acid ethyl ester.

32. A herbicide according to claim 4, wherein said N-acyl-N-phenyltetrahydrophthalamic acid derivative is N-(2-chloroacetyl)-N-(4-chloro-2-fluoro-5-isopropoxyphenyl)-3,4,5,6-tetrahydrophthalamic acid ethyl ester.

33. A herbicide according to claim 4, wherein said N-acyl-N-phenyltetrahydrophthalamic acid derivative is N-(2-chloroacetyl)-N-(4-chloro-2-fluoro-5-methoxyphenyl)-3,4,5,6-tetrahydrophthalamic acid isopropyl ester.

34. A herbicide according to claim 4, wherein said N-acyl-N-phenyltetrahydrophthalamic acid derivative is N-(2-chloroacetyl)-N-(4-chloro-2-fluoro-5-methoxyphenyl)-3,4,5,6-tetrahydrophthalamic acid propargyl ester.

35. A herbicide according to claim 4, wherein said N-acyl-N-phenyltetrahydrophthalamic acid derivative is N-(2-chloroacetyl)-N-(4-chloro-2-fluoro-5-isopropoxyphenyl)-3,4,5,6-tetrahydrophthalamic acid propargyl ester.

36. Method of producing N-acyl-N-phenyltetrahydrophthalamic acid derivatives represented by the general formula (I), as defined above, the method comprising the following steps in sequence:

(a) reacting anilide derivatives represented by the general formula (V) with a dehydrochlorinating agent so as to produce imidoylchloride derivatives represented by the general formula (II); and (b) reacting said imidoylchloride derivatives with a carboxylic acid represented by the general formula (III), without isolating and refining said imidoylchloride derivatives, in the presence of a base,

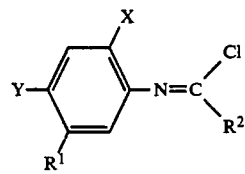

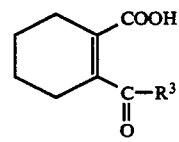

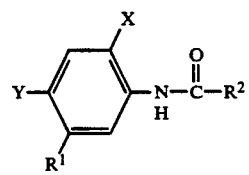

wherein X, Y, $R^1$, $R^2$ and $R^3$ are as defined hereinabove.

* * * * *